US00PP12176P2

(12) United States Plant Patent
Hill, Jr.

(10) Patent No.: US PP12,176 P2
(45) Date of Patent: Oct. 30, 2001

(54) GUZMANIA PLANT NAMED 'ANTON'

(75) Inventor: Herbert H. Hill, Jr., Lithia, FL (US)

(73) Assignee: Twyford Plant Laboratories, Inc., Sebring, FL (US)

( * ) Notice: Subject to any disclaimer, the term of this patent is extended or adjusted under 35 U.S.C. 154(b) by 0 days.

(21) Appl. No.: 09/586,793

(22) Filed: Jun. 5, 2000

(51) Int. Cl.[7] ..... A01H 5/00
(52) U.S. Cl. ..... Plt./371

(58) Field of Search ..... Plt./371

*Primary Examiner*—Bruce R. Campell
*Assistant Examiner*—June Hwu
(74) *Attorney, Agent, or Firm*—Foley & Lardner

(57) ABSTRACT

A new Guzmania plant named 'Anton' particularly distinguished by its tall, purple bracted inflorescence. Plants of 'Anton' are of small to intermediate stature and are best grown in 10-cm to 12.5-cm pots. Plants of 'Anton' grow vigorously and produce exceptionally uniform crops. It tolerates a wide range of cultural conditions and is easy to grow.

1 Drawing Sheet

BACKGROUND OF THE INVENTION

The present invention comprises a new and distinct cultivar of Guzmania plant, hereinafter referred to by the cultivar name 'Anton'. The genus Guzmania is a member of the family Bromeliaceae.

Guzmania comprise a genus of over 100 species of herbaceous evergreen perennials suitable for cultivation in the home or under glass. Guzmania are predominantly epiphytic with a few terrestrial species and are native to the tropics. For the most part the species vary in diameter from 7 to 8 inches to 3 or 4 feet and have rosettes of glossy, smooth edged leaves.

Floral bracts of Guzmania frequently have brilliant colors and may last for many months. The range of flower colors for Guzmania is generally from the yellow through orange but may also include flame red and red-purple. White or yellow, tubular, three petalled flowers may also appear on a stem or within the leaf rosette but are usually short lived.

Guzmania may be advantageously grown as potted plants for greenhouse or home use. Desirably the plants are shaded from direct sunlight during the spring to autumn period, the central vase-like part of the leaf rosette is normally filled with water.

Guzmania is native to tropical America. Leaves of the Guzmania are usually formed as basal rosettes which are stiff and entire and in several vertical ranks. Guzmania have terminal spikes or panicles which are often bracted with petals united in a tube about as long as the calyx.

Asexual propagation of Guzmania is frequently done through the use of tissue culture practices. Propagation can also be from off-shoots which are detached from the mother plant, and may be grown in an appropriate soil or bark mixture.

The new cultivar 'Anton' is the product of a planned breeding program and was originated by the inventor, Herbert H. Hill, Jr., from a cross made during such program in Lithia, Fla. in May of 1992. The female or seed parent is Guzmania 'Ultra' (U.S. Plant Pat. No. 8,221). The male or pollen parent is a proprietary selection of *Guzmania wittmackii*. The selection comprising the new variety was chosen after commencement of flowering in October of 1995.

The new cultivar was asexually propagated by off-shoots by the inventor in Lithia, Fla. beginning in January 1996. Asexual propagation by tissue culture was initiated in March of 1996. Continuous asexual propagation has demonstrated that the combination of characteristics as herein disclosed for the new cultivar 'Anton' are firmly fixed and are retained through successive generations of asexual reproduction.

BRIEF DESCRIPTION OF THE INVENTION

The following traits have been repeatedly observed and are determined to be basic characteristics of 'Anton' which in combination distinguish this Guzmania as a new and distinct cultivar:

1. Inflorescence is tall, upright and dark-purple in color;

2. Foliage is dark olive-green and is flushed or streaked with purple on the undersides of the leaves. It is also resistant to leaf tip browning and leaf spotting;

3. Inflorescence is durable, and can remain attractive with good color for at least 8 weeks in indoors; and, 4. Plants are best adapted to smaller pot sizes 10–12.5 cm.

'Anton' has not been observed under all possible environmental conditions. The phenotype of the new cultivar may vary significantly with variations in environment such as temperature, light intensity, and daylength without any change in genotype.

Of the many commercial cultivars known to the present inventor, the most similar in comparison to 'Anton' is the parental cultivar 'Ultra', which is characterized by its dark-purple inflorescence. In comparison to 'Ultra', the inflorescence of 'Anton' is considerably taller. The leaves of Anton are flushed with purple and are uniformly darker-green than the leaves of 'Ultra'.

In comparison to the male parental cultivar *Guzmania wittmackii*, 'Anton' produces a tall purple bracted inflorescence, though not at tall as the red-orange bracted scape of *Guzmania wittmackii*. The brackets of 'Anton' are shorter, broader, and more closely spaced that those of *G. wittmackii*.

BRIEF DESCRIPTION OF THE DRAWING

The accompanying photographic illustration shows a 12-month-old 'Anton' plant following growth under appropriate growing conditions, with colors being as true as possible with illustrations of this type. The illustration depicts a side view of the inflorescence and foliage characteristics of 'Anton' grown from an off-shoot in a 12-cm pot.

DETAILED BOTANICAL DESCRIPTION

The following observations, measurements and values describe 12 month old plants grown in Lithia, Fla., under greenhouse conditions which closely approximate those generally used in horticultural practice. Color references are made to The Royal Horticultural Society Colour Chart (R.H.S), except where general colors of ordinary significance are used.

Classification: Commercial: *Guzmania hybrid* cv. 'Anton'.

Parentage:

*Male parent.*—Proprietary selection of *Guzmania wittmackii.*

*Female parent.*—*Guzmania hybrid* cv. Ultra.

Propagation: Vegetative, by removal of offsets.

Plant:

*Form.*—Basal rosette of closely layered strap-like leaves arranged around a short central stem.

*Height.*—Approximately 43–48 cm when flowering.

*Diameter.*—Approximately 47–52 cm.

*Growth habit.*—Vigorous.

Foliage:

*Size.*—The basal leaves are approximately 27 cm–32 cm long and 2.3 cm–3.0 cm wide (flattened). At their widest point near the base, the leaves are approximately 4.7 cm to 5.4 cm wide.

*Shape.*—The leaf blade is ligulate with an acute tip. The leaf blade is channeled. The margins are entire. The leaves are curved outward over their length.

*Surface texture.*—The leaf blade is stiff and leathery, with a glossy surface.

*Color.*—The leaves are dark-green throughout the foliage. The undersides of the leaves are dark-green in base color, flushed and striated with purple. The upper surface is darker than, but closest to, RHS 137A, and the lower surface is greener than, but closest to, RHS 137A, often flushed and striated with RHS 187A.

*Average number.*—The plant produces approximately 24 leaves before producing an inflorescence.

Bracts:

*Length width color.*—The bracts vary in length, the upper-most terminal bracts being approximately 6 cm long and 2 cm wide. The color of both the upper and lower surfaces of most terminal bracts is RHS 59C, becoming RHS 150D at the base. The primary bracts which cover branch spikes are approximately 11.5 cm to 13.5 cm long, and 2.5 cm to 3.0 cm wide. The base of the primary bract at the attachment point to the scape may be approximately 5 cm in width. The color of both the upper and lower surfaces of the largest most colorful primary bracts is RHS 59A to RHS 59B, becoming green RHS 145D to RHS 146C at the base. There are vertical stripes present on both upper and lower surfaces, RHS 59B. The scape bracts are approximately 14 cm to 24 cm in length and 2.5–3.0 cm wide. The base of the scape bract at the attachment point to the scape may be approximately 4.5 cm in width. The color of both the upper and lower surfaces of the scape bracts is RHS 137A at the tip, becoming purple RHS 59B to RHS 59C, with RHS 145D to RHS 146C at the base. There are vertical stripes present on both upper and lower surfaces, RHS 59B.

*General shape/arrangement.*—The bracts are lanceolate with acute tips, and are arranged in closely spaced vertical ranks along the inflorescence.

*Number.*—Terminal Bracts: Approximately 10. Primary Bracts: Approximately 12. Scape Bracts: Approximately 9.

*Texture* (*both upper and lower surfaces*).—Terminal Bracts: Smooth and leathery, somewhat coreaceous. Primary Bracts: Smooth and leathery, somewhat coreaceous. Scape Bracts: Smooth and leathery, somewhat coreaceous.

*Margin.*—Terminal Bracts: Entire. Primary Bracts: Entire. Scape Bracts: Entire.

*Scape.*—The scape is approximately 45 cm tall, approximately 10 mm in diameter, and RHS 145A to RHS 145C in color.

Branch spikes: The inflorescence contains branch spikes which protrude from under primary bracts, each containing approximately 8 flowers. The bracts of the branch spikes are similar in color and dimension to the terminal bracts.

Inflorescence:

*Borne.*—Terminal in the inflorescence and in branch spikes.

*Individual flowers.*—Approximately 105 flowers or flower buds present, terminal in the inflorescence concealed under bracts. Calyx: Gamosepalous, three sepals present approximately 3.2 cm long and 4 mm wide, translucent white, RHS 155B in color; smooth surface texture; margin is entire. Corolla: Gameopetalous, three petals present approximately 4.9 cm long and 0.5 cm wide, white, RHS 155A in color; smooth surface texture; margin is entire.

*Time of blooming.*—In mature plants, flowering begins approximately 13–16 weeks after induction, at any time of the year.

*Duration of inflorescence.*—The inflorescence will hold its color approximately 2–3 months. Individual flowers last 1 day, and the total duration of flowering is about 6 weeks.

Reproductive organs:

*Ovary.*—Superior, three locules, 6 mm long, RHS 145D in color.

*Style.*—4.3 cm long, RHS 155A in color.

*Stamens.*—Six present, filament 4.1 cm long, anthers 5.5 mm long, RHS 11B in color.

Roots: Roots are greenish-white, changing to brown, wiry with fine laterals.

Seed charactertistics: Sterile F1 hybrid.

Pest/disease susceptibility: Typical of Guzmania plants, no particular susceptibility to common pests or disease.

Other observations: The plant appears to be more tolerant than averge to leaf tip browning and leaf spotting caused by marginal culture practices or poor water quality.

I claim:

1. A new and distinct cultivar of Guzmania named 'Anton', as illustrated and described.

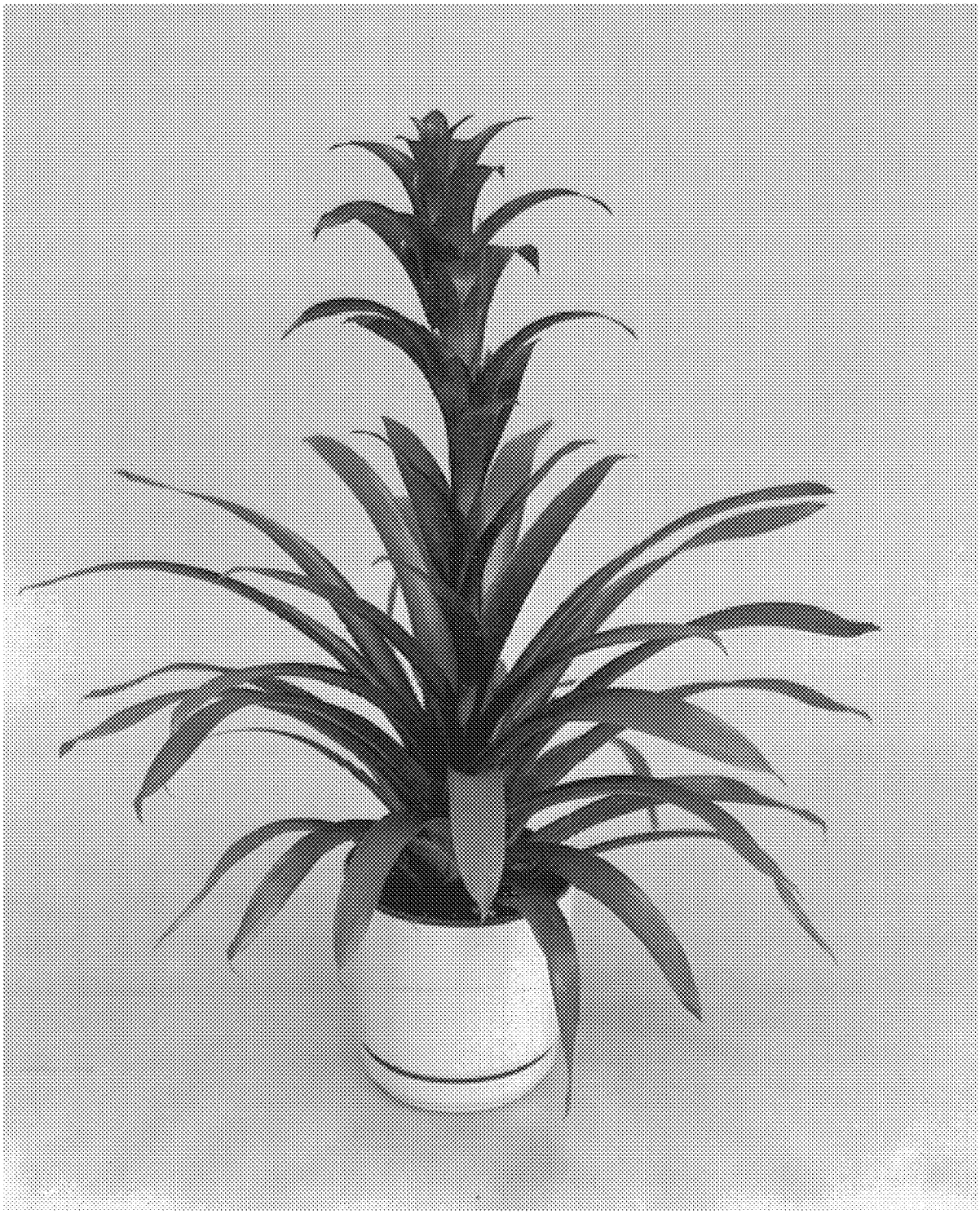

* * * * *